US00PP22797P3

(12) United States Plant Patent
Torn

(10) Patent No.: US PP22,797 P3
(45) Date of Patent: Jun. 19, 2012

(54) ***GARDENIA* PLANT NAMED 'BAB1183'**

(50) Latin Name: *Gardenia jasminoides*
Varietal Denomination: BAB1183

(75) Inventor: Douglas I. Torn, Brown Summit, NC (US)

(73) Assignee: Buds & Blooms Nursery, Inc., Brown Summit, NC (US)

( * ) Notice: Subject to any disclaimer, the term of this patent is extended or adjusted under 35 U.S.C. 154(b) by 0 days.

(21) Appl. No.: 12/807,567

(22) Filed: Sep. 8, 2010

(65) Prior Publication Data

US 2012/0060247 P1 Mar. 8, 2012

(51) Int. Cl.
*A01H 5/00* (2006.01)

(52) U.S. Cl. ..... Plt./255

(58) Field of Classification Search ..... Plt./255
See application file for complete search history.

(56) References Cited

U.S. PATENT DOCUMENTS

PP15,189 P3 9/2004 Barendse ..... Plt./255

*Primary Examiner* — Annette Para
(74) *Attorney, Agent, or Firm* — MacCord Mason PLLC

(57) ABSTRACT

A new and distinct variety of *Gardenia jasminoides* called 'BAB1183' is shown and described. The plant is produces large, double flowers and is cold hardy.

3 Drawing Sheets

Genus and species name: The present invention relates to a new and distinct gardenia variety of *Gardenia jasminoides*.

Variety denomination: This new and distinct *Gardenia* variety is identified as 'BAB1183'.

BACKGROUND

*Gardenia* plants are native to various tropical and subtropical regions around the planet. Because of their tropical and subtropical origins, *Gardenia* plants tend to thrive in warm humid environments such as USDA Zones 8 or 9. *Gardenia* plants are not typically recommended for zones colder than zone 7. Others have attempted to develop more cold hardy *Gardenia* plants. *Gardenia jasminoides* 'Frostproof' is one such example. 'August Beauty' is another example of a commercially available *Gardenia* with some cold hardiness. The 'BAB1183' is distinguishable from known *Gardenia* by, at least, its large flowers. The 'BAB1183' may also be distinguishable for any of the reasons below.

SUMMARY OF THE INVENTION

This new and distinct *Gardenia* variety is identified as 'BAB1183', and has a compact, semi-dwarf habit with very large, double, fragrant flowers and large, evergreen foliage. The 'BAB1183' is hardy in USDA Zones 6-10; exhibits extreme hardiness to 0° F. or colder; and is extremely drought tolerant and pest resistant. The 'BAB1183' is also strong and fast growing, reaching a mature height of 4 to 5 feet in approximately 15 years.

The 'BAB1183' is distinguished from all other varieties of *Gardenia* known to the inventor by at least one of its cold hardiness; large bloom; compact, semi-dwarf habit; and glossy leaves. The 'BAB1183' may also be distinguishable for other reasons as well.

A comparison between BAB1183, AUGUST BEAUTY (not patented) and CROWN JEWEL (U.S. Plant Pat. No. 19,896):

TABLE 1

| PARAMETER | BAB1183 | AUGUST BEAUTY | CROWN JEWEL |
|---|---|---|---|
| USDA Zones | 6-10 | 8-11 | 7 |
| Cold Hardiness (Extreme) | 0° F. | 15° F. | −15° C. (5° F.) |
| Immature Upper Leaf Texture | High-glossy | Glossy | Glabrous with thick, waxy cuticle layer |
| Mature Leaf Texture | Smooth, extremely glossy | High-glossy | Glabrous with thick, waxy cuticle layer |
| Corolla Length | 5 cm | 3 cm | 2.0-2.5 cm |
| Corolla Width | 9.5-11.4 cm | 5-8 cm | 1 cm |
| Floral Type | Double | Double | Double |

Applicant plans to market the 'BAB1183' as the Summer Snow Gardenia.

BRIEF DESCRIPTION OF ILLUSTRATIONS

The file of this patent contains at least one photograph executed in color. Copies of this patent or patent application publication with color drawings(s) will be provided by the office upon request and payment of the necessary fee.

DETAILED BOTANICAL DESCRIPTION OF THE PLANT

Figure 1:
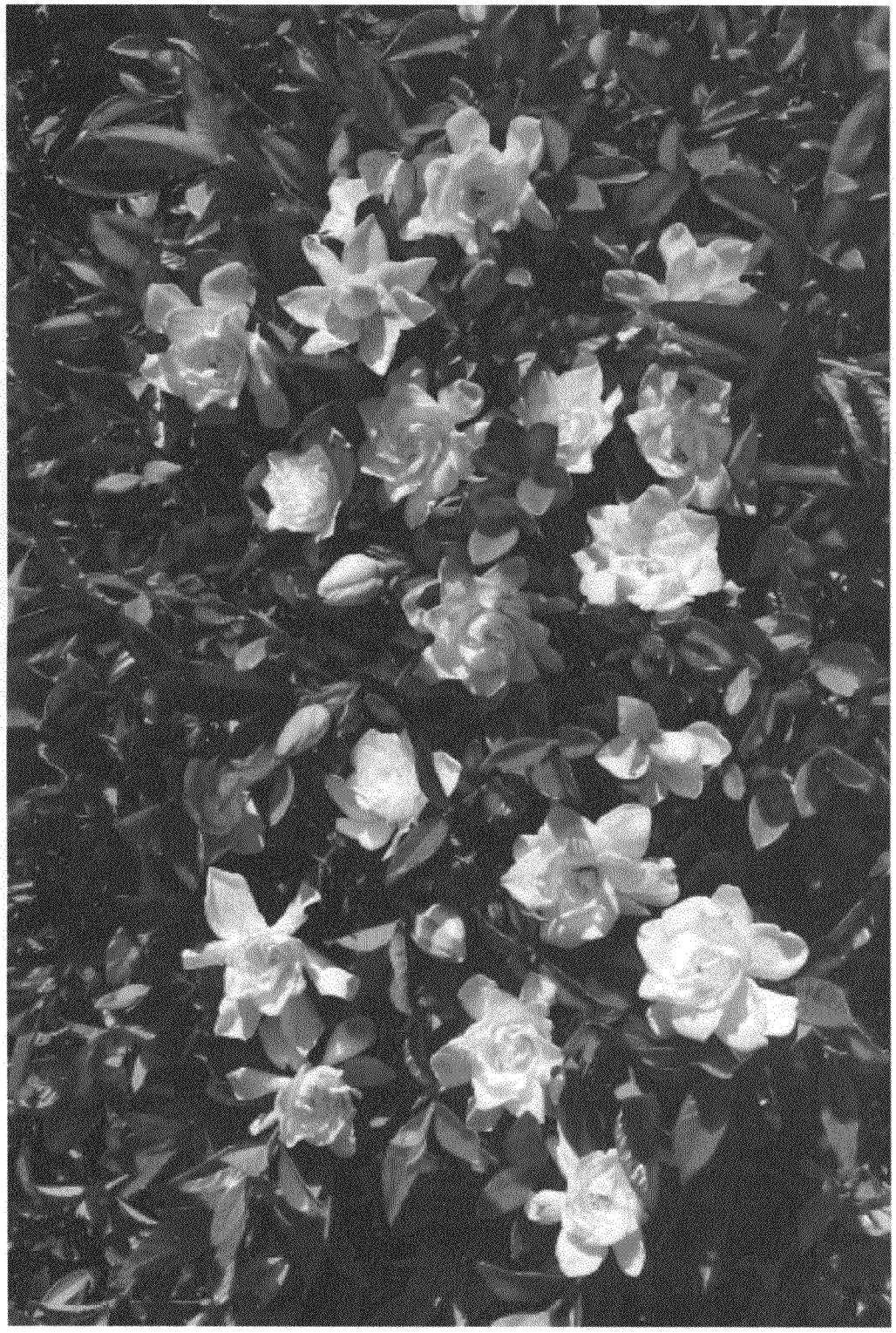
FIG. 1 is a photograph of the above-ground biomass of the novel variety of *Gardenia* identified as 'BAB1183'.
Figure 2:
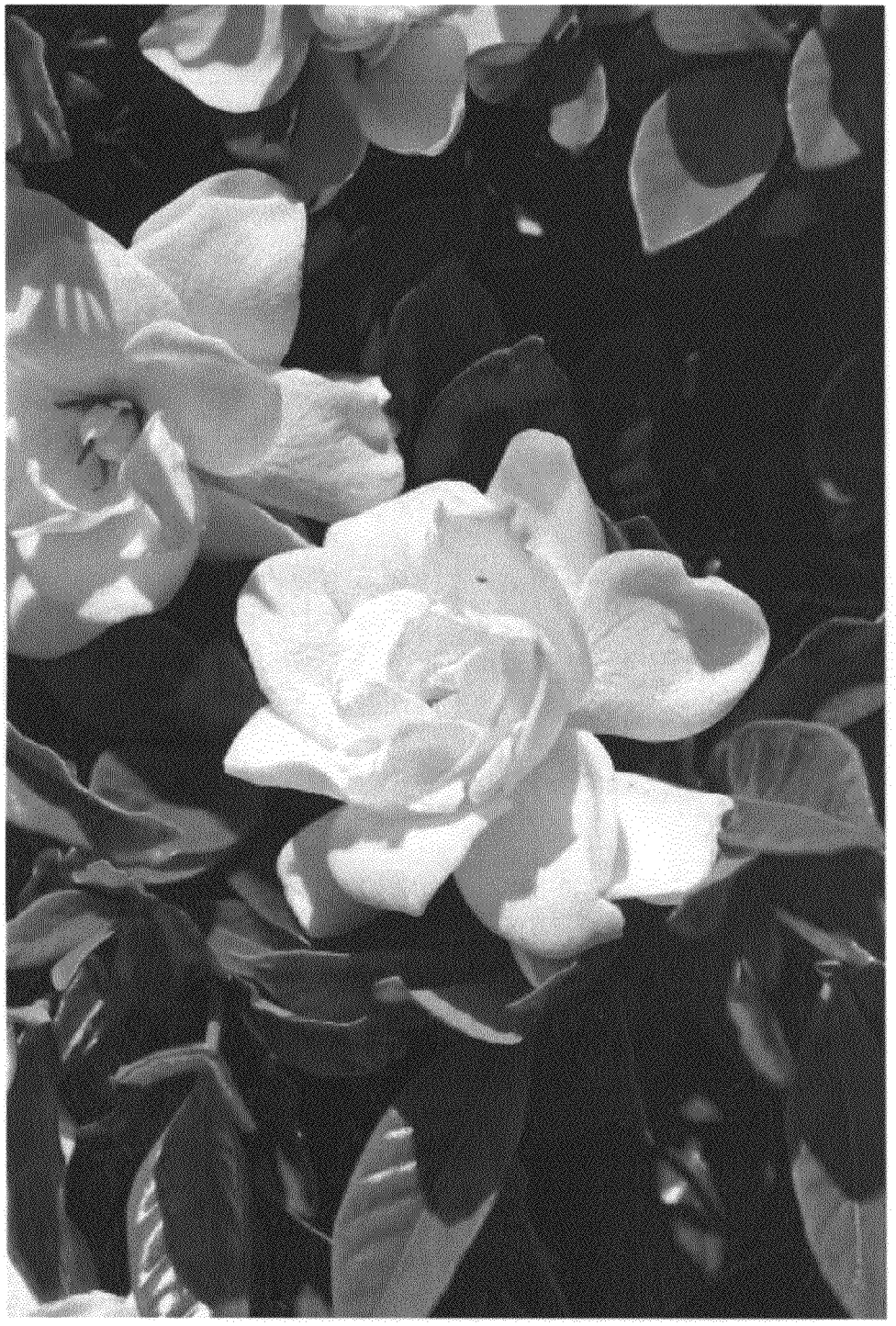
FIG. 2 is a close-up photograph of a flower of the 'BAB1183' plant.
Figure 3:
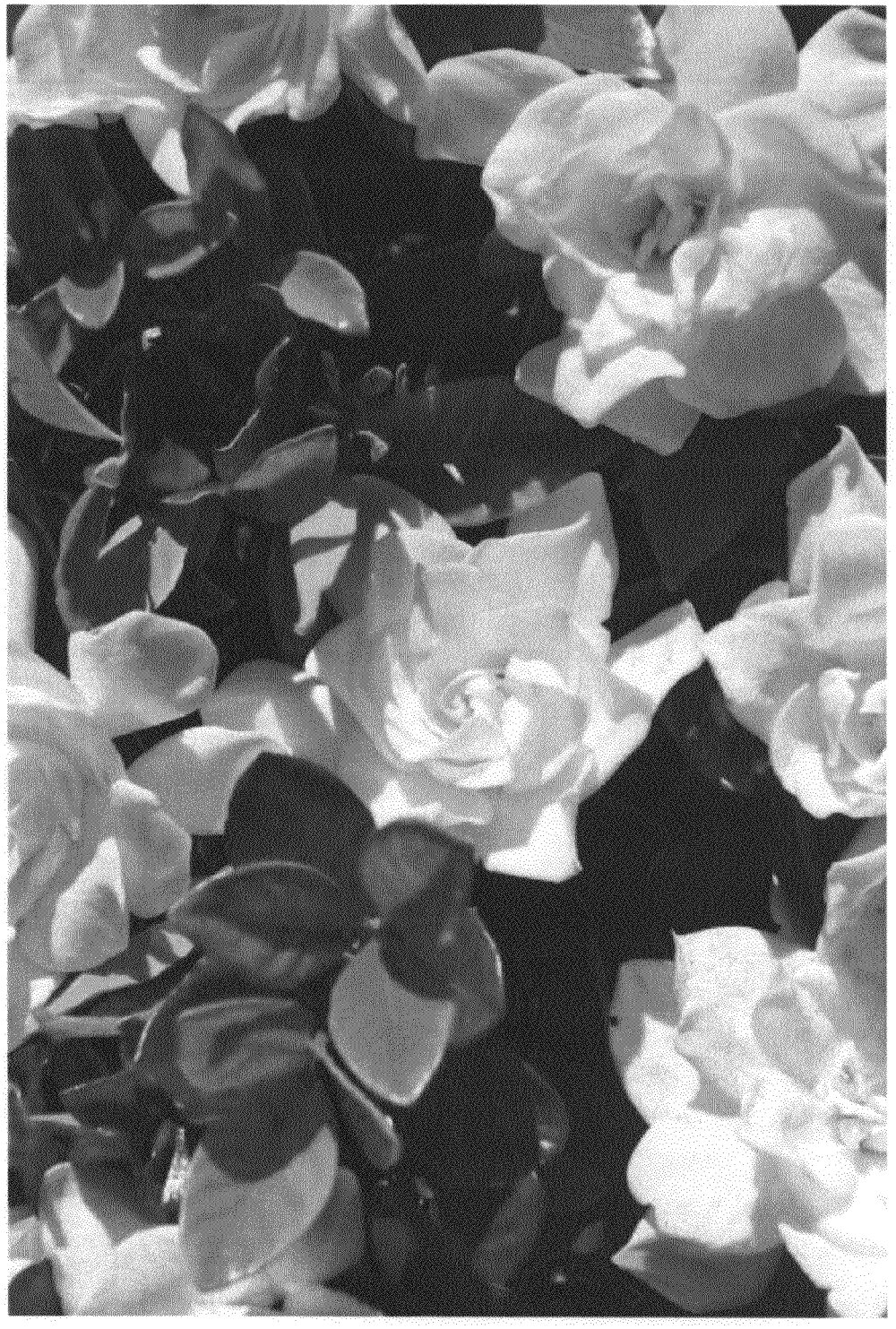
FIG. 3 is a close-up photograph of leaves from the 'BAB1183' plant.

Origin: In approximately 1993, the Inventor obtained vegetative cuttings from what the inventor believes to be a hybrid plant of unknown parentage in a cultivated sandy garden in Dania, Fla., located in Broward County, USDA Zone 10. Cuttings were grown and plants were selected for sturdiness for approximately 14 seasons in USDA Zone 7 (Guilford County, North Carolina) in an outdoor area. Plants exhibiting high levels of sturdiness in USDA Zone 7 were selected for outdoor growth in USDA Zone 6. After selection following approximately 2 growing seasons in USDA Zone 6, the inventor discovered the unique characteristics of the 'BAB1183'.

Asexual Reproduction: The 'BAB1183' has been asexually reproduced using vegetative cuttings by the inventor in Guilford County, NC. The 'BAB1183' has also been asexually reproduced, for the inventor, through micropropagation. Asexual production of the 'BAB1183', by the inventor, has shown that the unique features of this *Gardenia* are stable and the plant reproduces true to type in successive generations of asexual propagation.

A detailed description of the *Gardenia jasminoides* 'BAB1183' follows. All measurements were taken from a representative two year old plant grown outdoors in Guilford Co., North Carolina. (USDA Zone 7). The Inflorescence description is based on a flower opened for approximately 2 days in the month of June. Colors are based on The Royal Horticultural Colour Chart. When dimensions, sizes, colors, etc. are given, it should be understood that such characteristics are approximations set forth as accurately as possible. Variations may occur under other growth conditions based on, for example, climatic factors, fertilization, pruning, pest control, etc.

Classification:

*Botanical.*—*Gardenia jasminoides* 'BAB1183'.

*Propagation.*—Vegetative cuttings.

Plant:

*Hardiness.*—USDA Zone 6-10, with extreme hardiness to 0° F.

*Size.*—122 cm high, 122-152 cm wide.

*Habit.*—Young plants are upright/open becoming upright/dense with age.

*Form.*—Rounded.

*Branching.*—Dichotomous, branching freely from vegetative and reproductive buns in second year.

*Flowering response.*—Terminal flowers appear at branch tips.

*Flowering season.*—The majority of the blooms are from June to July, with periodic, isolated blooming Spring through the Fall.

*Rooting habit.*—Freely branched, fine roots.

Immature leaf—lower:

*Surface texture.*—Glabrous.

*Surface pubescence.*—None present, Glabrous.

*Surface color.*—Yellow-Green 146C.

Immature leaf—upper:

*Surface texture.*—High-glossy.

*Surface pubescence.*—None present, Glabrous.

*Surface color.*—Yellow-Green 144A.

Leaf—mature:

*Shape.*—Elliptic.

*Base.*—Acuminate.

*Apex.*—Acute to acuminiate.

*Size.*—Length 10.2 cm, width 4.4 cm.

*Arrangement.*—Opposite and whorled.

*Margin.*—Entire.

*Texture/substance.*—Smooth, extremely glossy.

*Mature leaf color.*—Lower, Green 146B; upper, Green 137A and Green 139A.

*Midvein pattern.*—Pinate.

*Midvein color.*—Yellow-Green 144B.

*Petioles.*—Length 1.9 cm, diameter 0.3 cm, shape rounded-top slightly flattened.

*Petioles color.*—Yellow-Green 144A.

Stems:

*Internode length.*—5.2 cm.

*Pith.*—Solid.

*Young stem color.*—Start Yellow-Green 144A, turns Yellow-Green 146B turns Grey-Brown N199B.

*Young stem diameter.*—0.4 cm.

*Young stem pubescence type.*—Scabrous, color Yellow-Green 144A.

Vegetative buds:

*Scale number.*—Three.

*Number at node.*—Two or three at leaf node.

*Size.*—3 mm long at longest point. 1 mm wide at widest point.

*Position/disposition.*—Flat relative to stem.

*Type.*—Valvate.

Inflorescence:

*Floral size.*—Corolla length, 5 cm. Corolla width, 9.5 cm-11.4 cm.

*Floral color.*—Petal upper and lower surfaces, White 155C. Fading bloom color for petal upper and lower surfaces, White 155a.

*Floral type.*—Double.

*Petal size.*—Length, 3.8 cm. Width, 2.5 cm.

*Petal shape.*—Apex rounded, base fused, margin entire, texture matte.

*Petal pubescence type.*—Grabrous.

*Bloom duration.*—7 days per bloom (approx.).

*Sepal size.*—Length, 2.5 cm. Width, 0.2 cm.

*Sepal shape.*—Folded over, apex acute, base fused, margin entire.

*Sepal texture.*—Matte to semi-glossy.

*Flower bud pedicel.*—Length, 1.3 cm-1.9 cm.

*Flower bud pedicel pubescence type.*—Glabrous.

*Flower bud pedicel color.*—Yellow-green 144A.

*Stamen.*—Number, 5. Length, 1.3 cm. Anther color, Greyed-Yellow 161C.

*Pollen color.*—Greyed-Yellow 161C.

What is claimed is:

1. A new and distinct variety of *Gardenia jasminoides* plant, substantially as herein described and illustrated.

* * * * *